United States Patent [19]

Quick et al.

[11] 4,041,122

[45] Aug. 9, 1977

[54] PROCESS FOR MOLDING OF HOLLOW ARTICLES

[75] Inventors: James R. Quick; William A. Wittosch, Jr., both of Warwick, N.Y.

[73] Assignee: International Paper Company, New York, N.Y.

[21] Appl. No.: 691,470

[22] Filed: June 1, 1976

[51] Int. Cl.$^2$ ................................................. B29C 1/06
[52] U.S. Cl. .................................... 264/277; 264/275; 264/278; 264/328
[58] Field of Search ................ 264/275, 277, 278, 328

[56] References Cited

U.S. PATENT DOCUMENTS

| | | | |
|---|---|---|---|
| 2,314,262 | 3/1943 | Winder | 264/154 |
| 2,367,235 | 1/1945 | Morin | 264/328 X |
| 2,465,799 | 3/1949 | Gravesen | 264/328 X |
| 3,142,716 | 7/1964 | Gardener | 264/278 X |
| 3,311,690 | 3/1967 | Fischer | 264/278 |
| 3,363,040 | 1/1968 | Aoki | 264/278 |
| 3,442,987 | 5/1969 | Sentementes | 264/343 X |
| 3,477,101 | 11/1969 | Fritsch | 264/328 X |
| 4,005,166 | 1/1977 | Quick | 264/328 X |

Primary Examiner—Richard R. Kucia
Attorney, Agent, or Firm—Richard M. Barnes

[57] ABSTRACT

Disclosed is a process for the molding of hollow articles such as full length Foley catheters. The apparatus preferably comprises a mold with two lumen forming wires longitudinally disposed therein. A set of two receiving wires are spaced distally from the distal ends of the lumen forming wires and are longitudinally aligned therewith. A first follower is slidably disposed about the lumen forming wires in close abutment with the wires and inside wall of the mold. The first follower is preferably disposed toward the proximal end of the mold and preferably at least two other followers are provided spaced distally of the first follower. One of the other followers preferably bridges the space between the lumen forming wires and receiving wires. Sets of gates are preferably provided along the length of the mold in fluid communication with a source of molding material. In practice, molding material is injected into the molding channel at the proximal end of the mold and flows longidutinally toward the distal end of the mold while pushing the first follower along the wire ahead of it. As the follower proceeds toward the distal end of the mold, it engages and pushes the remaining followers toward the distal end of the mold. At the beginning of the molding process, each set of gates has a follower that is transversely aligned with it so as to seal the set of gates and prevent the flow of molding material through the set of gates and into the mold. In this fashion, molding material is not introduced through a set of gates and into the mold until all followers are distally located from the set of gates.

14 Claims, 10 Drawing Figures

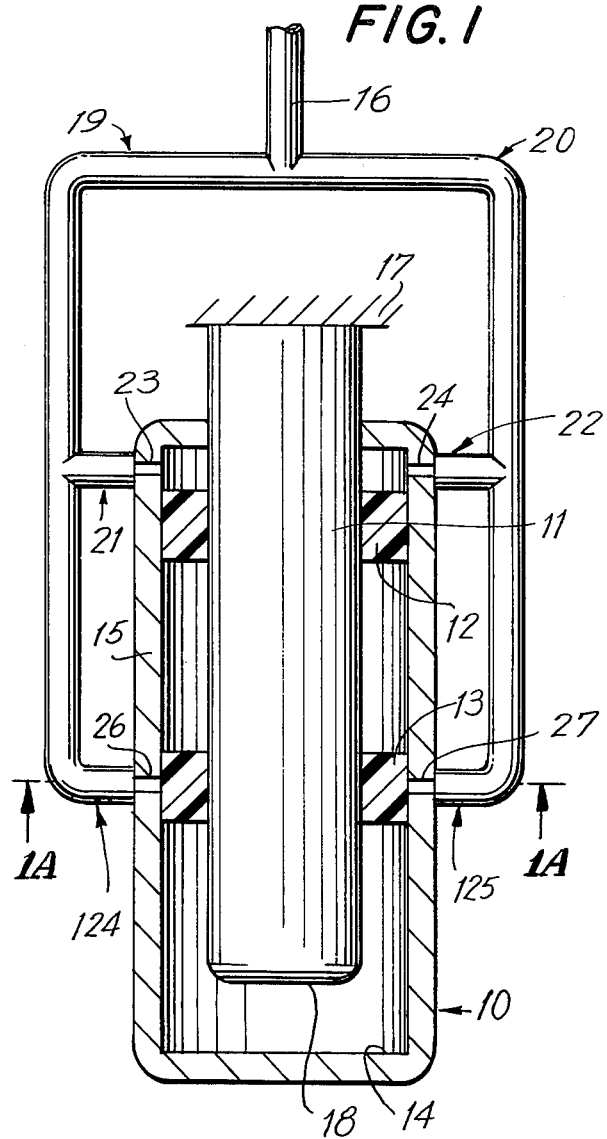
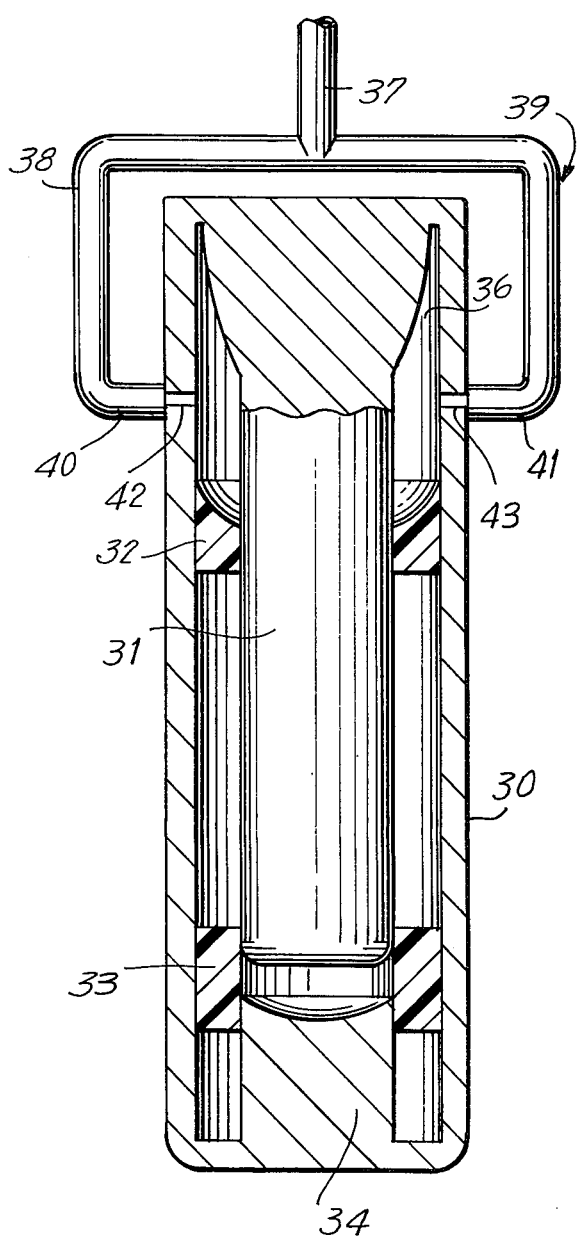
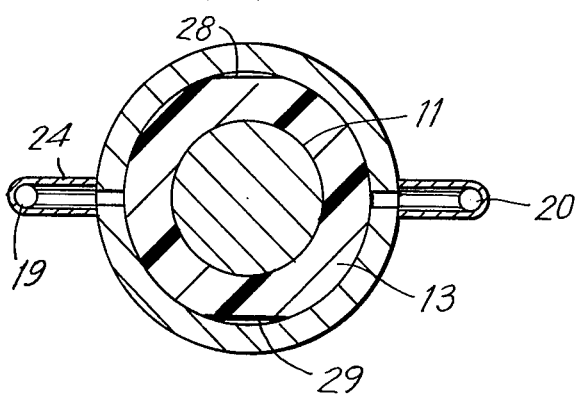

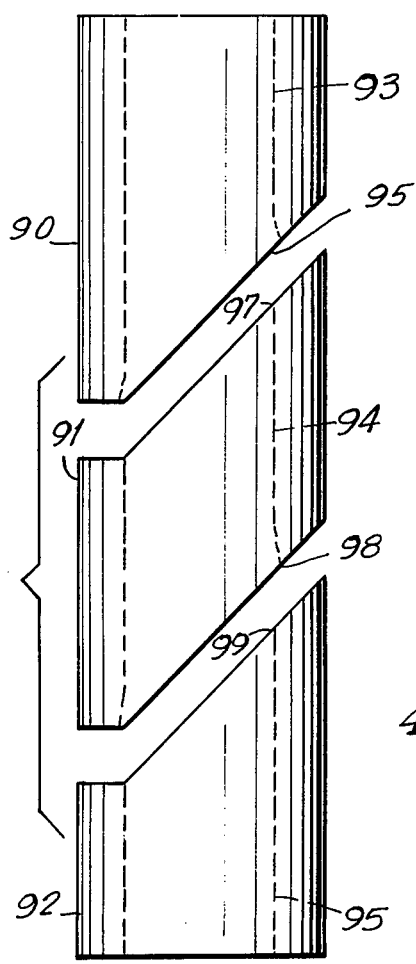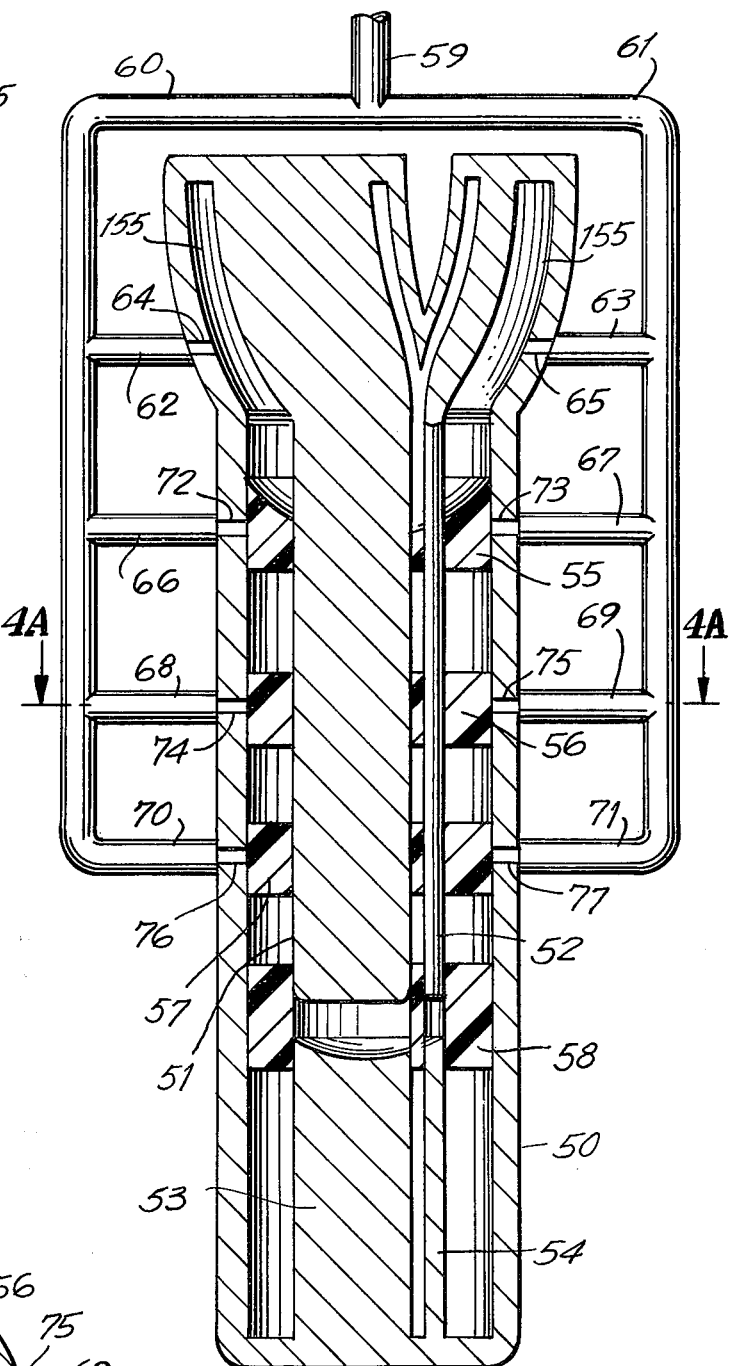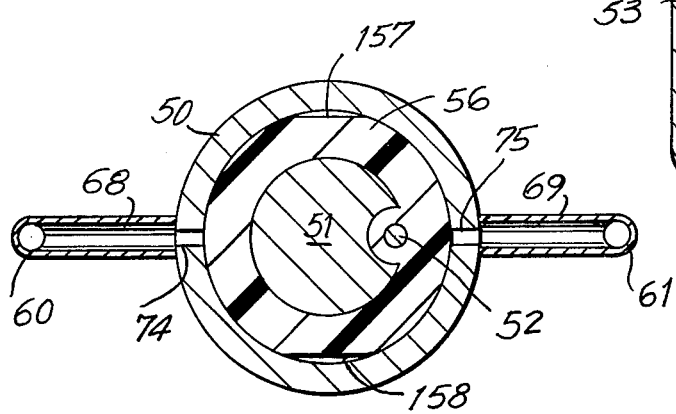

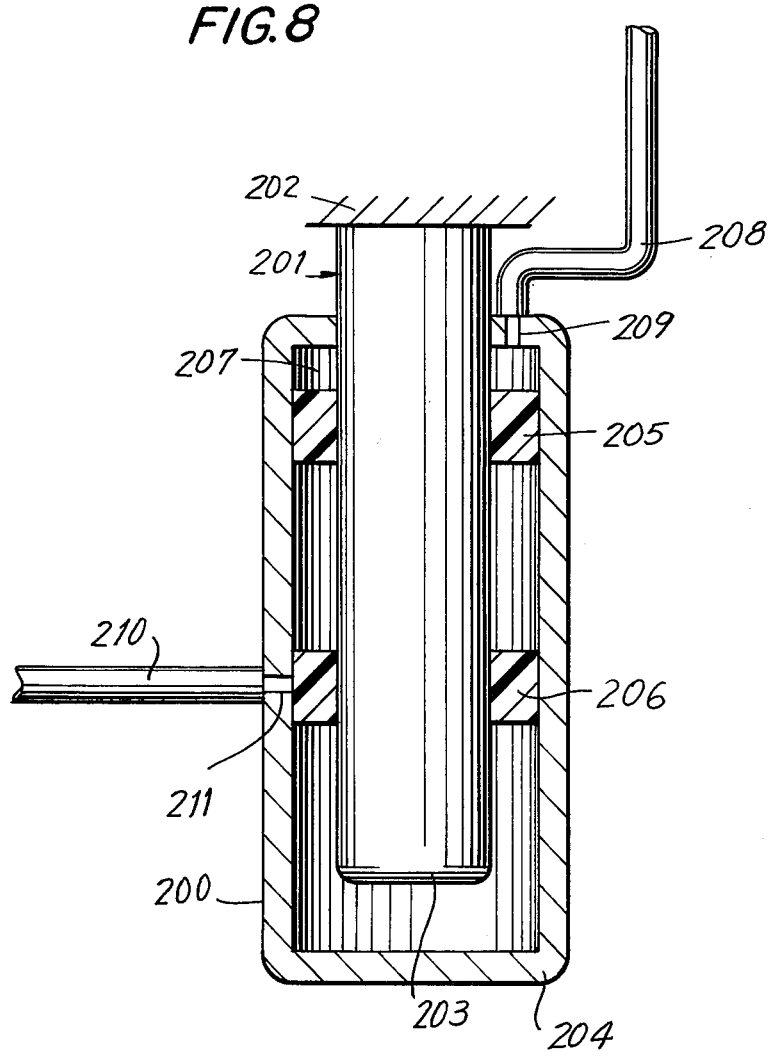

PROCESS FOR MOLDING OF HOLLOW ARTICLES

BACKGROUND OF THE INVENTION

This invention relates to a molding process for producing hollow articles, particulary full length Foley catheters. In the past, hollow articles have been produced by a variety of dipping, molding and extrusion apparatus and processes. However, each of these prior art processes and apparatus have suffered from disadvantages that are substantially overcome by the present apparatus and process.

In the dipping processes known in the prior art, a wire is dipped into a liquified material to be formed into the hollow article. With each dip of the wire more product from the bath adheres to the coated wire until eventually the desired amount of material is built up onto the wire. Then the material coated on the wire is sufficiently hardened so as to permit the hollow article surrounding the wire to be peeled or stripped therefrom. One disadvantage of the dipping process is the large number of dips and great amount of time sometimes required to build up the desired amount of material on the wire. Additionally, when the hollow article to be manufactured requires small diameter wires, many materials are too viscous in a liquified state for the wire to be dipped therein without bending of the wire.

As with the above described prior art dipping processes, other prior art processes also have disadvantages. For instance, extrusion processes are not advantageously employed to obtain products with a closed end. Further, while many molding processes may be employed to obtain products with closed ends, these processes are generally not advantageously employed when the article is relatively long and slender. The reason for this is that the portion of the mold defining the hollow portion of the final product is often unstable and bends at the high pressures employed in the molding process.

The above noted deficiencies in prior art processes and apparatus are substantially overcome by the process and apparatus disclosed in U.S. Pat. application Ser. No. 580,881, filed May 27, 1975. The apparatus of the above-noted application comprises a mold cavity with a first wire longitudinally disposed therein. A second wire may be spaced distally from the distal end of the first wire in longitudinal alignment therewith. Upon injection of molding material into the mold, said material flows longitudinally toward the distal end of the mold cavity pushing the follower ahead of it. When the follower reaches the distal end of the first wire, it continues to move distally in the mold onto the second wire thereby bridging the gap between the first wire and the second wire. Eventually, the follower disengages entirely from the first wire to provide a hollow article with a solid tip. If a hollow article without a solid tip is desired, only one wire is used and the follower does not disengage from the wire.

The process described in the above-noted application has two disadvantages. First, it is difficult to produce long articles with relatively small hollow portions according to the process and apparatus disclosed because the small wire required is distorted by the high pressures required. For example, full length Foley catheters can not be produced by the process and apparatus disclosed in U.S. application Ser. No. 580,881 because the small inflation lumen wire is distorted by the high process pressure required to such an extent that the wire touches the mold wall to provide a useless inflation lumen with a hole in it. Second, when a hollow article with a solid tip is produced according to the process and apparatus of the above-noted application, the follower is transferred from a first wire to a second wire. However, the first wire may be twisted with respect to the second wire by the high pressures required, thereby preventing the smooth transfer of the follower from the first wire to the second wire. As described in U.S. application Ser. No. 580,881, the seriousness of this problem may be diminished by using specially designed followers and second wires in which the cross sectional area defined by the inside wall of the distal end of the follower is larger than the cross sectional area defined by the proximal end of the second wire. However, the specially designed follower and second wire of the above-noted application may not always accomplish their intended function, and at any rate, an apparatus and process that do not require a specially designed follower and second wire would be most desirable.

The process of the present invention may be used to produce hollow articles from a wide variety of materials, including materials which are too viscous in a liquid state to be used to produce hollow articles by prior art dipping processes. Additionally, the process and apparatus of the present invention may be employed to produce hollow products with one of the ends closed by a solid tip. Further, the process and apparatus of the present invention may be used to produce long articles with relatively small, long hollow portions, such as Foley catheters. Finally, the process of the present invention may be used to produce hollow articles with a solid tip without requiring the use of a specially designed follower and second wire.

SUMMARY OF THE INVENTION

The apparatus of one embodiment of the present invention comprises a mold with at least a first wire longitudinally disposed therein. First and second followers are slidably disposed about the first wire in close abutment with both the wire and inside wall of the mold. A set of gates in fluid communication with a source of molding material is provided in the walls of the molds. At the beginning of the molding process, the second follower is spaced distally of the first follower and is positioned to seal the set of gates. Molding material is then introduced through a gate into the annular space defined by the wire and inside of the mold proximally of the proximal end of the first follower. The molding material thus introduced into the annular space flows longitudinally toward the distal end of the mold while pushing the first follower along the wire ahead of it. As the follower proceeds toward the distal end of the mold, the first follower reaches the second follower and pushes it toward the distal end of the mold. As the first follower proceeds to push the second follower distally, the followers will eventually no longer seal the set of gates. At such time, molding material will flow into the annular space through the gates thereby pushing the followers toward the distal end of the mold. It will be appreciated by those skilled in the art that process pressures are reduced by providing multiple inlets into the mold as described above. The lower process pressures required, in turn, reduce distortion of the wire in the mold.

In a second embodiment of the invention, a hollow article with a solid tip may be produced. In the second embodiment, there is provided a second wire spaced distally from the distal end of a first wire and longitudinally aligned therewith. A first follower is slidably disposed about the first wire in close abutment with the first wire and inside of the mold. A second follower is provided which bridges the gap between the first wire and second wire. Molding material is then injected through a gate into the annular space defined by the first wire and the mold and flows longitudinally toward the distal end of the mold while pushing the first follower ahead of it. As the follower proceeds along the wire toward the distal end of the mold, the first follower reaches the second follower and proceeds to push the second follower toward the distal end of the mold. Eventually, the first follower disengages from the first wire and entirely engages with the second wire. Because the first follower is substantially aligned with the second follower when they first touch, the transfer from the first wire to the second wire may frequently be smooth. However, the transition from the first wire to the second wire may be facilitated by notching the first follower and second follower so that they will not twist with respect to each other once they are engaged.

It is within the scope of the present invention to employ both a follower which initially seals gates and a follower which bridges wires in the same apparatus. Additionally, multiple wires may be employed to provide articles with multiple hollow portions therein. The above noted features are concurrently used in the most preferred embodiment of the present invention to produce a full length Foley catheter.

To produce a full length Foley catheter, there is provided a mold with drainage lumen and inflation lumen wires longitudinally disposed therein. Two receiving wires are spaced distally from the distal ends of the drainage lumen and inflation lumen wires and are longitudinally aligned therewith.

Preferably three followers are slidably disposed about the drainage lumen and inflation lumen wires in close abutment with the wires and inside wall of the mold, and a fourth follower is positioned so that it bridges the space between the lumen wires and receiving wires. The four followers are preferably about evenly spaced between widened funnel forming portions of the lumen wires and the end of the lumen wires. The first three followers located along the longitudinal axis of the mold are initially transversely aligned with three sets of opposing gates. As noted supra, the fourth follower bridges the space between the lumen wires and the receiving wires.

In operation, molding material is introduced into the mold through a gate proximally of the first follower. The molding material then flows toward the distal end of the mold pushing the first follower ahead of it. As the follower is pushed distally, the first set of gates which was initially sealed by the first follower is opened and molding material flows into the molding channel through these gates.

The first follower continues toward the distal end of the mold in response to the pressure of molding material injected through the first set of gates until the first follower meets and engages with a second follower. The two followers then continue together distally in the mold until the second set of gates is no longer sealed. Thereafter, molding material flows into the molding channel through the second set of gates.

We have found that if at least two sets of gates are not employed when producing a full length Foley catheter, the inflation lumen wire is distorted by the forces in the mold until it touches the wall of the mold. This, of course, results in a useless inflation lumen with holes in it.

Moreover, to insure wire stability, it is preferred that a third follower and a third set of gates be used in the mold. Initially the third follower is aligned with and seals a third set of gates in the same fashion described above in connection with the first two followers. After the first three followers have proceeded in the mold cavity past the third set of gates, eventually, the distal end of the third follower reaches and engages the proximal end of the fourth follower. Unlike the previous three followers, the fourth follower is not transversely aligned with a set of gates but, rather, bridges the space between the drainage lumen and inflation lumen wires and the receiving wires. In this fashion it is insured that the lumen forming wires are aligned with the receiving wires at the time the proximal end of the fourth follower disengages from the lumen forming wires.

To insure that the lumen forming wires and the followers remain aligned with the receiving wires as the followers proceed through the space between the lumen wires and receiving wires, the followers may be interlockingly notched so that they will not twist with respect to each other. Thus, if the lumen wires or any follower is twisted slightly in response to process pressures, then all the followers and the proximal ends of the receiving wires are twisted in the same fashion to insure that the followers remain aligned with the receiving wires.

As the followers continue to proceed distally in the mold, eventually the first follower disengages totally from the drainage lumen and inflation lumen wires and continues distally until finally it is totally engaged with the receiving wires. In this fashion, molding material is permitted to flow inwardly across the entire cross section of the mold between the distal end of the drainage lumen and inflation lumen wires and the proximal ends of the receiving wires thereby forming the solid tip of the Foley catheter. Desirably, the proximal ends of the first follower and the receiving wires are concave so as to provide a rounded, smooth tip.

During the molding process the mold is preferably maintained at a suitable temperature so that shortly after the followers reach the distal end of the mold the molding material will be cured or hardened. After the molded material is sufficiently cured or hardened, the mold is opened and the hollow article is stripped or peeled from the lumen forming wires. Molding material will also have hardened in the gates and inputs thereto in the mold. This material may be easily removed from the catheter by a cutting operation either before or after the catheter is peeled from the lumen forming wires. Thereafter, holes are provided in the catheter in communication with the drainage and inflation lumens by conventional techniques. Finally, a balloon is attached near the distal end of the catheter to obtain the completed Foley catheter.

The number of followers used in the present invention may be increased indefinitely until a substantial portion of the mold is filled with followers, in which case it is preferred to use a single continuous follower. The single continuous follower functions substantially in the same manner as the followers described above, except that it may simultaneously block more than one set of gates and bridge the space between lumen wires and receiving wires.

BRIEF DESCRIPTION OF THE DRAWINGS

FIG. 1 shows the mold employed in one embodiment of the present invention.

FIG. 1A shows a cross section of FIG. 1 along line 1-A—1-A.

FIG. 2 shows the mold employed in another embodiment of the invention.

FIG. 3 shows three notched followers about to engage one another used in the preferred embodiments of the present invention.

FIG. 4 shows the mold used to manufacture Foley catheters according to a preferred embodiment of the present invention.

FIG. 4A shows a cross-section of FIG. 4 along lines 4A—4A.

FIG. 8 shows the mold used in another embodiment of the present invention.

DESCRIPTION OF THE PREFERRED EMBODIMENTS

Figure 5:
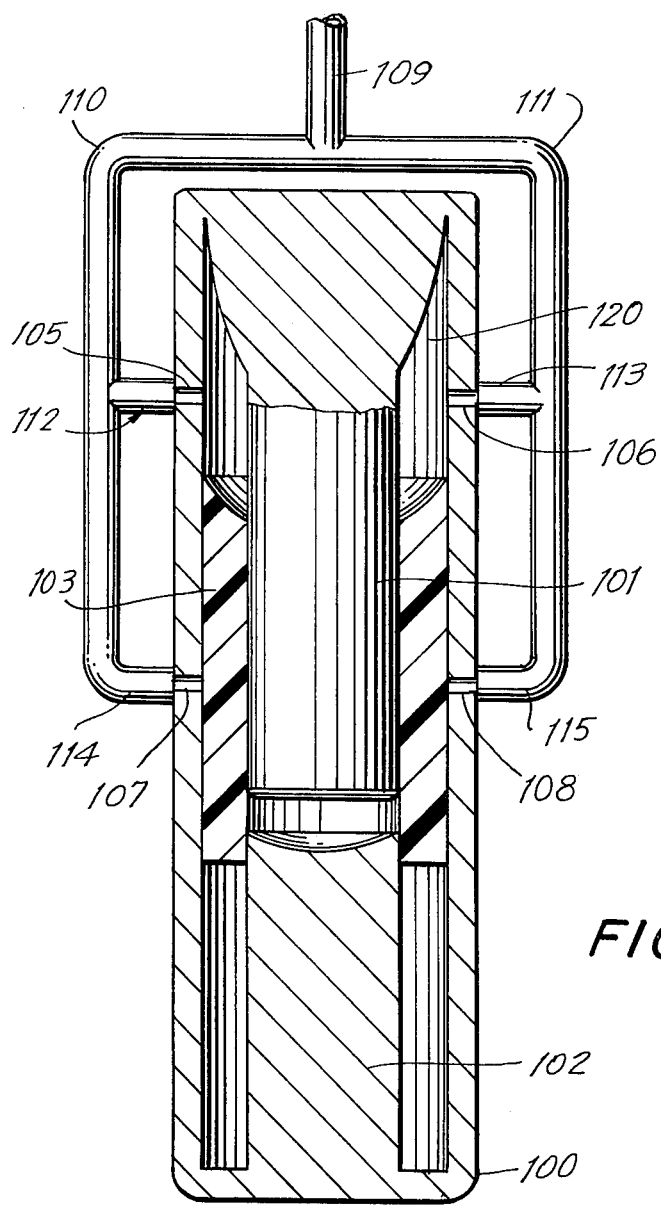
FIG. 5 shows another embodiment of the present invention.

Referring to FIG. 1, there is shown in cross section mold 10 with wire 11 and followers 12 and 13 provided therein. As shown in FIG. 1, wire 11 is hung from a source 17 and terminates at 18 close to the distal end 14 of mold 10. However, it is to be understood that any suitable means for providing the wire in the mold may be used in the invention. For instance, the wire 11 may be imbedded into or adhesively attached to the distal end 14 of mold 10.

As shown in FIG. 1, followers 12 and 13 fit snugly into the annular space 15 in close abutment with wires 11 and the inside wall of mold 10. As described more fully in U.S. application Ser. No. 580,881, the followers 12 and 13 fit into the mold 10 so that in use the followers will not move prematurely or permit the flow of material into the spaces between the followers 12 and 13 and the inside wall of mold 10 or wire 11.

At the start of the process, molding material is injected from a source (not shown) through line 16 to two runners 19 and 20 that extend along opposed sides of the mold. Runners 19 and 20 are preferably identically designed and symmetrically oriented with respect to the mold 10 so that in use, the flow of molding material will be substantially the same in each runner. As molding material proceeds to flow along the runners 19 and 20, eventually some of the molding material will flow via lines 21 and 22 through gates 23 and 24 into annular space 15 proximally of follower 12.

While opposed gates 23 and 24 are used to introduce molding material proximally of first follower 12 in the embodiment shown in FIG. 1 (and in other embodiments described below), it is to be understood that a single gate may be used to introduce molding material proximally of follower 12. It is further to be understood that the source of molding material for each gate 23 and 24 (and for the other gates used in this embodiment and other embodiments described below) need not be the same as shown in FIG. 1.

The molding material injected into the mold 10 flows through annular space 15 pushing follower 12 ahead of it until the distal end of follower 12 reaches the proximal end of follower 13. In the meantime runners 19 and 20, as well as lines 124 and 125 and gates 26 and 27, have been filled with molding material. Injection of molding material into the mold via gates 26 and 27 is prevented up to this point however, because follower 13 is initially positioned in the mold 10, as shown in FIG. 1, to seal gates 26 and 27. However, when follower 12 reaches follower 13, it continues along the mold pushing follower 13 ahead of it until eventually gates 26 and 27 are unsealed when the proximal end of follower 12 passes gates 26 and 27. At this time, molding material is injected into mold 10 via gates 26 and 27 and flows through annular space 15, pushing followers 12 and 13 toward the distal end 14 of mold 10.

In the embodiment shown in FIG. 1 and 1A (and in other embodiments described below) runners 19 and 20, lines 21, 22, 124 and 125, and gates 23, 24, 26 and 27 are preferably identically designed and symmetrically oriented with respect to mold 10. The reason for this is that when a small wire is used in the invention, it is important the the wire is not subjected to any pressure that might distort it. Therefore, gates 26 and 27 oppositely oppose each other at the same longitudinal distance along the mold as shown in FIGS. 1 and 1A so that opposing forces from material injected through the gates 26 and 27 tend to cancel each other out. It will be appreciated that when a small wire is used in the invention more than two gates may be suitably arranged symmetrically around the periphery of the mold within the scope of the present invention. Further, it will be appreciated that a ring gate enveloping the entire mold may be used pursuant to the present invention. Finally, it will be appreciated that in some circumstances, e.g., where thick wires are used, single gates may be used instead of sets of gates along the length of the mold. A single gate may also be used when it is desired to introduce molding material through the proximal end wall of the mold.

It should be recognized that the relative dimensions of the component parts of the mold assembly shown in FIG. 1 (as well as in FIGS. 2 and 4 to 6) are distorted for the purposes of illustration. In practice it is contemplated that the cross sectional area of runners 19 and 20 will be substantially larger than the cross sectional area of annular space 15. Thereby, the pressure drops that occur in the runners will be substantially lower than the pressure drops that occur in the mold itself with the result being that substantially lower pressures can be employed in molds that employ multiple sets of gates. The reduction of process pressures permitted by the apparatus and process of the present invention is particularly advantageous when small wires (e.g., 0.035 inch diameter), which can be easily distorted, are used.

It will be appreciated by those skilled in the art that the manner in which the gates are sealed by a movable follower is characterized by its relative simplicity. Other methods and means of sealing the gates, e.g., by valves actuated by pressure transducers, could be used, but these other methods and means would be much more complicated and costly than the method and means used in the present invention.

As was noted supra, the gates used in the present invention are preferably identically designed so that the forces exerted by molding material injected into the mold via the opposing gates end to balance each other. The preferred dimensions of the gate used, of course, will vary depending on the particular process and apparatus parameters employed, e.g., width of wires, length of the mold, molding material, etc. However, when producing Foley catheters, as described in more detail below, the gates are preferably 0.100 inch long and have a cross sectional area of 0.050 inch by 0.100 inch.

Preferably, each follower used in the present invention is provided with at least one air vent and most preferably two air vents 28 and 29, as shown in FIG. 1A. The purpose of these air vents is to relieve air pressure caused by the compression of the air space in the mold during the molding process. At least one air vent (not shown) is also located at the distal end of the mold. The design of the air vents is not particularly critical, but the vents 28 and 29 should preferably be out of alignment with gates 26 and 27, as shown in FIG. 1A, and should be small enough to prevent the passage of substantial amounts of molding material into the space defined by the vents 28 and 29 and the inside wall of the mold 10.

As is apparent from FIG. 1, when followers 12 and 13 reach the distal end of mold 10, follower 12 is still on wire 11. As a result, a hollow article with an open end is produced. However, it is to be understood that the mold may be designed so that both followers 12 and 13 disengage entirely from wire 11 to provide a hollow article with a pigtailed tip. As described in U.S. application Ser. No. 580,881, the pigtail on the tip results from molding material flowing into the holes provided in followers 12 and 13.

After follower 13 reaches the distal end of mold 10, the molding material is hardened by known processes. Thereafter, the mold is opened and the hollow article is stripped from the wire. When the molding material is catalyzed silicone rubber, it is desirable to heat the mold as described in U.S. application Ser. No. 580,881 to partially cure the molding material during the molding process.

Referring now to FIG. 2, there is shown an apparatus for producing a closed ended hollow article according to the present invention. More specifically, and for purposes of illustration, there is shown an apparatus for producing a nonretention urinary catheter.

Urinary catheters, as is well known to physicians, are used in the treatment of individuals who have lost control of their urinary function. One generally accepted medical practice involves inserting a tube or catheter into the urinary passage until the remote or distal end is located within the bladder. The near or proximal end of the catheter remains outside the body. Often the most proximal end of the catheter is in the shape of a funnel. The funnel is in communication with a path or drainage lumen that is provided along the longitudinal axis of the catheter. The distal end of the catheter contains a hole in communication with the drainage lumen such that in use the bladder may drain through the hole into the drainage lumen and out through the funnel into a suitable receptacle. While the invention is described with respect to urinary catheters, it is to be understood that other types of catheters, e.g., tracheal catheters, venous catheters, etc. operate on similar principles and may be manufactured according to the present invention.

As shown in FIG. 2, there is provided mold 30 with first wire 31 longitudinally disposed therein. A second wire 34 is also provided and is longitudinally aligned with the first wire. Wire 31 is attached to a suitable source which, as shown in FIG. 2, may be the proximal end of mold 30. As shown, the distal end of the first wire 31 is spaced from the proximal end of the second wire. The proximal end of the first wire 31 is preferably widened so that a catheter with a funnel at its proximal end is provided by the process of the present invention.

At the beginning of the molding process, a first follower 32 is preferably positioned a short distance from the widened portion of wire 31. A second follower 33 is positioned so that it bridges the space between the distal end of the first wire 31 and the proximal end of the second wire 34, as shown in FIG. 2. The followers 32 and 33 are again fitted snugly into annular space 36 closely abutting wires 31 and 34 and the inside of mold 30 as described above in connection with FIG. 1.

With the followers so positioned, molding material, e.g., catalyzed silicone rubber, is introduced into the mold from a source not shown via line 37, runners 38 and 39, lines 40 and 41 and gates 42 and 43. Again, for reasons discussed above in connection with FIG. 1, it is preferred that the runners, lines and gates are identically designed and symmetrically oriented with respect to mold 30, although such design and orientation is not essential when employing the relatively thick wires (about 0.150 inch diameter) used to form the drainage lumens of nonretention urinary catheters.

The catalyzed silicone rubber which has been injected into the mold via gates 42 and 43 flows through annular space 36 and pushes follower 32 ahead of it. Eventually, the distal end of follower 32 reaches the proximal end of follower 33. At this point, the follower 32 continues to slide along wire 31 in response to the pressure of injected silicone rubber pushing follower 33 ahead of it. Eventually, both the first follower 32 and second follower 33 are entirely disengaged from the first wire 31 so that molding material may spread throughout the cross section defined by the inner wall of mold 30 thereby providing a solid tip for the catheter. When the distal end of the second follower 33 reaches the distal end of mold 30, the movement of the two followers stops. At this point, desirably the rounded proximal edges of first follower 32 are aligned with rounded proximal end of second wire 34 as shown in FIG. 5 of U.S. application Ser. No. 580,881 to provide a continuous smooth tip for the catheter. To complete the molding process, the molding material is hardened, the mold is opened and the catheter is stripped or peeled from the wire 31 as described above in connection with the description of FIG. 1. Thereafter, at least one drainage hole is provided toward the distal end of the catheter in communication with the drainage lumen.

It will be appreciated by those skilled in the art that the proportions shown in FIG. 2 are not the proportions which would be employed normally in the manufacture of urinary catheters. That is, a typical urinary catheter may be about 16 inches long and about 0.24 inches in diameter.

The catalyzed silicone rubber composition used in this embodiment of the invention (as well as the other embodiments described herein) may be prepared in the same manner and from the same materials as described in United States application Ser. No. 580,881. Additionally, the silicone rubber is suitably injected at the same temperatures and pressures described in the above-noted application. Even further, the materials used for the wires and followers in all embodiments of the present invention are preferably the same as the materials used in the above-noted application.

In the above-noted application, a second follower 33 was not used to bridge the space between first wire 31 and second wire 34. Rather, a specially designed first follower was used to insure a smooth transition of the first follower 32 from the first wire 31 to the second wire 34. In the present invention, however, second follower 33 stabilizes the first wire 31 with respect to the second wire 34 thereby helping to insure the smooth transition of the first follower 32 from the first wire 31 to the second wire 34. As a result, specially designed followers, such as those described in the above-noted application, are not required in the present invention.

Figure 6:
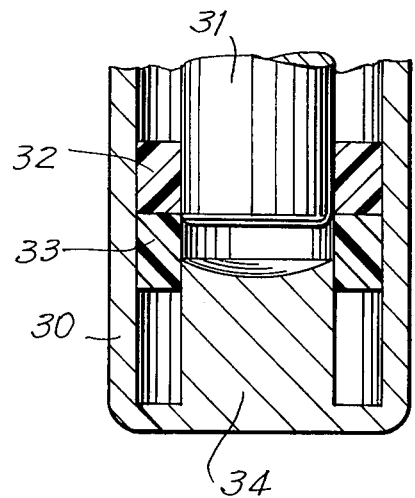
FIG. 6 shows the orientation of wires and followers at one time during the process using the apparatus shown in FIG. 2.

It will be appreciated by those skilled in the art that the embodiments shown in FIGS. 1 and 2 may be combined to give a process and apparatus with three or more followers. It will further be appreciated by those skilled in the art that when the wires and followers are oriented as shown in FIG. 6, the hole in the first follower 32 will be longitudinally aligned with second wire 34. That is, as long as the distal end of the first follower 32 is aligned with the distal end of wire 31, the first follower 32 will still be aligned with second wire 34. However, particularly when the wires are not concentric with the inner wall of the mold (as described infra in connection with FIG. 5), as the followers proceed distally in the mold beyond the orientation shown in FIG. 6, second follower 33 will no longer be engaged with the first wire 31 and therefore will be free to twist with respect to the distal end of first wire 31. As a result, the distal end of first wire 31 may no longer remain longitudinally aligned with the proximal end of second wire 34.

Thus, in the embodiment shown in FIG. 2, first follower 32 may become misaligned with the second wire 34 thereby preventing the smooth transition of the first follower 32 onto the second wire 34. The misalignment problem noted above may be overcome, however, by notching the followers used in the present invention so that they will interlock with each other thereby preventing the twisting of one follower with respect to another follower. One manner of interlockingly notching the followers is shown in FIG. 3.

Referring to FIG. 3, there is shown first follower 90, second follower 91 and third follower 92 arranged in the same order as they would be provided in a mold containing three followers. The followers are provided with holes 93, 94 and 95 represented by the dotted lines. It will be observed that the distal end of follower 90 and the proximal end of follower 91 are notched so that the followers 90 and 91 will engagedly interlock so that they can not twist with respect to each other. The distal end of follower 91 and the proximal end of follower 92 are similarly notched. In this fashion it is assured that once the followers are engaged with one another, they will not twist with respect to each other. This, in turn, insures the smooth transition of followers 90 and 91 onto the second wire.

The smooth transition of followers 90 and 91 onto the second wire may be further insured by tapering outwardly the distal ends of holes 93 and 94 as shown in FIG. 3. By so tapering the holes 93 and 94, the cross sectional areas defined by the inner walls of the distal ends of followers 90 and 91 are larger than the cross sectional area defined by the proximal end of the second wire. It is to be understood, however, that followers with tapered holes as described above are not part of the present invention per se but rather are part of the invention described in U.S. application Ser. No. 580,881. It is further to be understood that the taper in the inside walls of the followers used in the present invention need not be as great as the taper used in the above-noted application. The reason for this is that the use of notched followers, one of which initially bridges the first wire and second wire, largely diminishes or eliminates the need for specially designed inside walls in the followers used in the present invention.

Figure 7:
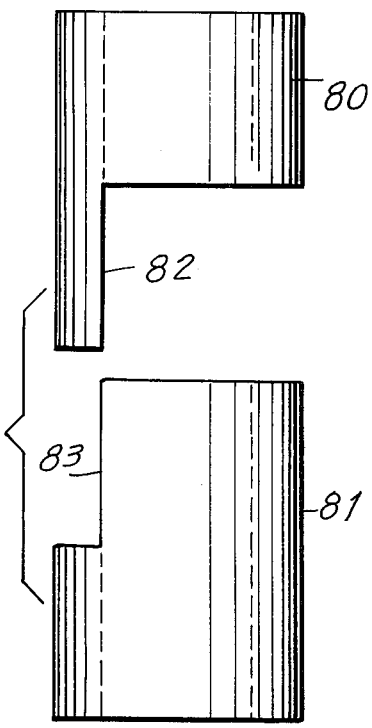
FIG. 7 shows two notched followers about to engage one another.

Before the notched followers 90-92 engage one another in the mold they may be twisted and turned with respect to each other due to forces in the mold. Referring now to FIG. 7, there is shown two followers 80 and 81 that are engagedly notched with respect to one another. However, it will be appreciated by those skilled in the art that if followers 80 and 81 are twisted with respect to each other in the mold they will not engage each other since the notches walls 82 and 83 of the followers are parallel to the longitudinal axis of the mold. It is therefore preferred in the present invention to angle the notched walls 96–99 of followers 90–92 with respect to the longitudinal axis of the mold as shown in FIG. 3. In this fashion the followers 90–92 will initially engage with one another even if the followers are twisted with respect to each other and self align as the engagement is completed.

As was noted supra in connection with the description of FIG. 2, non-retention urinary catheters may be produced according to one embodiment of the invention. However, one disadvantage of non-retention urinary catheters is that the patient using the catheter must remain essentially immobile while the non-retention catheter is inserted in him. Thus, generally, the catheter must be inserted into and removed from the patient each time the bladder is drained. As a result, it is generally preferred to use retention or Foley catheters which may conveniently remain in the patient for extended periods of time. Typically, retention is provided by including an inflatable balloon near the distal end of the catheter. During insertion, the balloon is deflated. After the distal end of the catheter is positioned within the bladder, the balloon is inflated by passing a fluid, typically water, through a passage within the catheter called an inflation lumen. When the balloon is inflated, the inflation lumen is sealed and the inflated balloon within the bladder insures retention. Thereafter the bladder drains through the drainage lumen provided in the catheter and running parallel to the inflation lumen.

Referring now to FIG. 4, there is shown an apparatus for producing a Foley catheter. More specifically, there is shown mold 50 with drainage lumen wire 51 and inflation lumen wire 52 provided therein. Spaced distally from the drainage lumen wire 51 and inflation lumen wire 52 and longitudinally aligned therewith are first receiving wire 53 and second receiving wire 54. Toward the proximal end of mold 50 the mold forks and the drainage lumen wire 51 and inflation lumen wire 52 widen so that the proximal end of the Foley catheter is provided with separate funnels in communication with the drainage and inflation lumens.

At the beginning of the molding process, a first follower 55 is positioned in molding channel 155 a short distance from the funnel portions of drainage lumen wire 51 and inflation lumen wire 52. At the beginning of the molding process, second and third followers 56 and 57 are positioned distally of the first follower, preferably at evenly spaced intervals along the length of the drainage lumen and inflation lumen wires 51 and 52. A fourth follower 58 is initially positioned to bridge the gap between the lumen wires 51 and 52 and first and second receiving wires 53 and 54. All followers are again fitted snugly into molding channel 155 closely abutting the lumen wires and receiving wires and the inside of mold 50 as described above in connection with FIGS. 1 and 2. Again, for purposes of illustration, the proportions shown in FIG. 4 are not the proportions which normally would be employed in the manufacture of Foley catheters.

To begin the molding process, material to be molded, e.g., catalyzed silicone rubber, is introduced into the proximal end of mold 50 from a source not shown via line 59, runners 60 and 61, lines 62 and 63 and gates 64 and 65. Only one gate is required for each wire in the two funnel forming sections at the proximal end of mold 50 since the wires at these locations are relatively stable and are not substantially displaced by injecting molding material through a single gate.

Runners 60 and 61 continue past lines 62 and 63 and are in fluid communication with lines 66 and 71, which in turn are in fluid communication with gates 72 and 77, respectively. At the beginning of the molding process, the followers are arranged with respect to gates 72 and 77 as shown in FIG. 4, i.e., follower 55 seals gates 72 and 73, follower 56 seals gates 74 and 75, and follower 57 seals gates 76 and 77.

As in the embodiments shown in FIGS. 1 and 2, the runners, lines and gates are preferably identically designed and symmetrically arranged with respect to the mold 50. The process and apparatus illustrated in FIG. 4 also works in substantially the same fashion as the embodiments shown in FIGS. 1 and 2. That is, the molding material introduced via gates 64 and 65 travels distally in the mold eventually reaching follower 55. Thereafter, molding material continues to travel distally in the mold pushing follower 55 ahead of it until gates 72 and 73 are no longer sealed. Thereafter, molding material is introduced into the mold via gates 72 and 73 in the same manner as material was introduced into mold 10 via gates 26 and 27 in the description of the embodiment shown in FIG. 1. Thereafter, followers 56 and 57 are moved distally and gates 74 and 77 are unsealed substantially as described above with respect to follower 55 and gates 72 and 73.

Eventually, follower 57 reaches follower 58 and the followers 55 to 58 proceed to transfer from drainage lumen wire 51 and inflation lumen wire 52 to first and second receiving wires 53 and 54. This transfer is substantially the same as the transfer of followers 32 and 33 from the first wire 31 to second wire 34 in the embodiment shown in FIG. 2 described above.

After the followers 55 to 58 have been pushed to the distal end of mold 50, the molding material is hardened, the mold opened, and the hollow article stripped from the wires as described above in connection with the embodiments shown in FIGS. 1 and 2. Thereafter, at least one drainage eye is provided toward the distal end of the catheter in communication with the drainage lumen. Additionally, at least one eye is provided in communication with the inflation lumen and a balloon is bonded to the catheter so that the inflation lumen is is in communication with the space defined by the catheter shaft and the inside of the balloon.

For convenience of illustration, the followers 55 to 58 shown in FIG. 4 are not interlocking. However, it is to be understood that the followers used in this embodiment are preferably the same type of interlocking followers shown in FIG. 3.

Referring now to FIG. 4A, there is shown a cross section of FIG. 4 along lines 4A—4A. It will be observed from FIG. 4A that while inflation lumen wire 52 is cylindrical, drainage lumens wire 51 preferably is not. Rather, drainage lumen wire 51 is cylindrical with a small arcuate section cut out. As is shown in FIG. 4A, inflation lumen wire 52 desirably is fitted into the space provided by the arcuate cut in drainage lumen wire 51. Thus, inflation lumen wire 52 and drainage lumen wire 51 are accommodated in a relatively small cross sectional area, and at the same time the drainage lumen produced has a desirable relatively large cross sectional area. As shown in FIG. 4A, follower 56 desirably has a set of air vents 157 and 158 similar to those shown in FIG. 1A.

As was noted, supra in connection with the description in FIG. 1, the runners, lines and gates are preferably identically designed and symmetrically arranged with respect to mold 50. The reason for this as noted supra is that by employing such a design and arrangement distortion of the wires in the mold is minimized. Such an effect is unexpected in the embodiment shown in FIG. 4A since inflation lumen wire 52 is much closer to gate 75 than it is to gate 74, and further since inflation lumen wire 52 is shielded from gate 74 by drainage lumen wire 51. It therefore might be expected that inflation lumen wire 52 would be distorted toward drainage lumen wire 51 in response to the pressure of molding material injected through gate 75. To the contrary, however, we have found that by using the arrangment of wires and gates shown in FIG. 4A, the inflation lumen wire remains stable.

While the reason why the arrangement of gates and wires shown in FIG. 4A works is not fully understood, it is known that when gates 74 and 77 are not employed in the embodiment shown in FIG. 4, the small, e.g. 0.035 inch diameter, inflation lumen wire 52 is distorted toward the inside wall of mold 50. This, of course, results in a useless Foley catheter with holes in the inflation lumen. It therefore appears that the arrangement of gates and wires shown in FIG. 4A in part counteracts the tendency that the inflation lumen wire 52 would otherwise have to distort outwardly toward the isinde wall of mold 50. It is also believed that the lower molding pressures permitted by the use of the gates as described above contributes to the stability of the wires.

In the embodiment shown in FIG. 4, there is provided three sets of gates which are initially sealed by three followers. However, a full length Foley catheter of the type described herein can be produced if one set of gates and its corresponding follower (preferably either gates 74 and 75 and follower 56 or gates 76 and 77 and follower 57) is eliminated. Of course, one set of gates but not its corresponding follower may be eliminated.

It is also to be understood that receiving wires 53 and 54 and follower 58 may be eliminated in producing a Foley catheter according to the present invention. When receiving wires 53 and 54 are not used, however, molding material flows into the holes in followers 55 and 57 at the distal end of the mold to provide a catheter with pigtails at its distal end. These pigtails must be removed, e.g. by cutting and polishing, before the catheter is inserted into the patient.

Additionally, it is to be understood that more than four followers may be provided in the mold 50 to provide additional stability to the wires provided therein. And, each additional follower may or may not be provided with a set of gates that are sealed by the follower at the beginning of the molding process.

It should also be understood that the number of followers and gates associated therewith may be increased in similar fashion in the embodiments of the invention shown in FIGS. 1 and 2. The number of followers used may be increased with followers, in which case it is preferred to use a single continuous follower as shown in FIG. 5.

Referring to FIG. 5, there is shown an apparatus for producing a closed ended hollow article, which for purposes of illustration may be a non-retention urinary catheter. As shown in FIG. 5, there is provided mold 100 with a first wire 101 lprovided therein. A second wire 102 is also provided spaced from the distal end of the first wire 101 and longitudinally aligned therewith. Wires 101 and 102 are attached to a suitable source which, as shown in FIG. 5, are the proximal and distal end of the mold 100, respectively. Toward the proximal end of the mold 100, first wire 101 widens so that the proximal end of the catheter produced is funnel shaped.

As noted, supra, the follower 103 spans a substantial portion, e.g. at least 50% and preferably at least 75%, of the first wire 101. At the beginning of the molding process, follower 103 is positioned as shown in FIG. 5. That is, the proximal end of follower 103 is located just distally of input gates 105 and 106 and extends the remaining length of first wire 101 to span the space between the first wire 101 and second wire 102. Another set of gates 107 and 108 is also provided along the length of the mold. Thus, the single follower 103 shown in FIG. 5 performs the dual function of initially sealing gates 107 and 108 and bridging the gap between first wire 101 and second wire 102 to insure the smooth transition of the proximal portion of follower 103 onto second wire 102.

To begin the process, molding material, e.g. catalyzed silicone rubber, is introduced into annular space 120 via line 109, runners 110 and 111, lines 112 and 113 and gates 105 and 106 at the proximal end of mold 100. The runners, lines and gates are again preferably, but not essentially, identically designed and symmetrically oriented with respect to mold 100. The silicone rubber pushes follower 103 distally in the mold thererby unsealing gates 107 and 108. Thereafter, molding material is introduced into the mold via gates 107 and 108 and follower 103 continues to move distally in the mold. Eventually, follower 103 totally disengages from the first wire 101 to entirely engage second wire 102 and subsequently reaches the distal end of the mold 100. Thereafter the silicone rubber is cured, the mold is opened, and the non-retention urinary catheter is stripped from wire 101 as described above.

It will be understood by those skilled in the art that a follower similar to the one shown in FIG. 5 can be used to produce a full length Foley catheter. In such case, a single continuous follower would be used in place of followers 55, 56, 57 and 58 in FIG. 4.

It will be recalled that it was noted supra, that molding material may be introduced into the mold through the proximal end of the mold. Further, it was noted supra that in appropriate circumstances molding material may be introduced into the mold through single gates instead of through sets of gates along the length of the mold. Finally, it was noted supra that the source of molding material need not be the same for each gate in the mold.

Referring now to FIG. 8 there is shown a mold 200 which incorporates each of the features noted immediately above. As shown in FIG. 8, wire 201 is hung from a source 202 and terminates at 203 close to the distal end 204 of the mold 200. As shown in FIG. 8, followers 205 and 206 fit into annular space 207 in close abutment with wire 201 and the inside wall of mold 204.

At the start of the molding process, molding material is introduced into the mold 200 from a source (not shown) through line 208 and gate 209. The molding material flows through annular space 207 pushing follower 205 ahead of it unitl the distal end of follower 205 reaches the proximal end of follower 206. In the meantime molding material has been introduced from a source (not shown) into line 210 and gate 211. Injection of molding material into the mold through gate 211 is prevented up to this point however, since follower 206 is initially positioned in the mold 200, as shown in FIG. 8, to seal gate 211. However, after follower 205 reaches follower 206 both followers are pushed distally through the mold in response to the pressure of molding material injected through gate 209. Eventually, gate 211 is unsealed when the proximal end of follower 205 passes gate 211 and thereafter, molding material is injected into mold 200 through gate 211. Thereafter followers 205 and 206 are pushed to the distal end of the mold 200 and the hollow article so produced is stripped from wire 201 as described above in connection with the other embodiments of the present invention.

With respect to all the embodiments described above, it will be appreciated that all the molding material in the mold will harden during the curing process. As a result, the hollow article stripped from the wire will have appendages corresponding to the shape of the gates, lines, etc. of the mold. To obtain a usefull article, these appendages must be cut from the hollow article. The imperfections at the cut points may then be polished. Alternatively, the hollow article may be dipped a few times into a dispersion of polymer material and hardened to cover the imperfections on the surface of the molded hollow article.

As was noted supra, the clearances used in the present invention should be maintained so that molding material will not flow either between the follower and inside of the mold or between the follower and wires. When using catalyzed silicone rubber, clearances of about 0.0015 inch have given good results although it is contemplated that clearances of up to 0.002 inches or even 0.005 inches could be used. At these clearances, generally the followers will not move prematurely. However, various devices may be used to insure that the followers remain properly positioned in the mold. For example, the followers, the wall of the mold, or both, may be magnetized. Additionally, rectracting pins activated by mechanical means or by electrical solenoids may be used. Or, a vacuum may be applied through the walls of the mold. Finally, an uncured silicone rubber adhesive may be used to maintain the followers in the proper position in the mold.

While the present invention has been described with respect to certain preferred embodiments, variations and equivalents may be perceived by those skilled in the art while nevertheless not departing from the scope of the invention as described by the claims appended hereto.

We claim:

1. The process of manufacturing a hollow article which comprises:
   a. providing a mold with a first wire longitudinally disposed therein and containing first and second followers disposed about the first wire in close abutment with both the first wire and inside wall of the mold, said followers maintaining the first wire spaced from the inside wall of the mold so as to define an annular space between the first wire and the inside wall of the mold;

b. positioning the second follower proximally of the distal end of the mold and spaced distally from the first follower thereby sealing a set of gates provided in the mold;

c. introducing a molding material under pressure into said annular space proximally of the proximal end of the first follower thereby distally displacing the first follower;

d. continuing the distal displacement of the first follower thereby engaging the second follower and, thereafter, distally displacing both the first and second followers thereby unsealing the set of gates;

e. thereafter introducing molding material into the annular space through the set of gates to continue the distal displacement of the followers while material is molded around the first wire; and f. stripping the resulting hollow article from the first wire.

2. The process of claim 1 which further comprises:

a. providing at least a third follower in close abutment with the first wire and inside wall of the mold;

b. positioning the third follower proximally of the distal end of the mold and spaced distally from the second follower; and c. continuing the distal displacement of the first and second followers until the third follower is engaged and thereafter distally displacing the first, second and third followers.

3. The process of claim 2 wherein the distal displacement of the three followers unseals a second set of gates, previously sealed by the third follower and, thereafter, introducing molding material into the annular space through the second set of gates.

4. The process of claim 1 which further comprises:

a. providing a second wire spaced distally from the first wire and longitudinally aligned therewith;

b. bridging the space between the first and second wires with a third follower, said third follower partially engaged with the first and second wires; and c. continuing the distal displacement of the first and second followers until the third follower is engaged and, thereafter, distally displacing the three followers off the first wire and onto the second wire whereby there is formed a hollow article with a solid tip.

5. The process of manufacturing a hollow article with a solid tip which comprises:

a. providing a mold with a first wire longitudinally disposed therein and containing a first follower disposed about the first wire in close abutment with both the first wire and the inside wall of the mold, said first follower maintaining the first wire spaced from the inside wall of the mold so as to define an annular space between the first wire and the inside of the mold;

b. providing a second wire spaced distally from the first wire and longitudinally aligned therewith;

c. bridging the space between the first wire and the second wire with a second follower;

d. introducing a molding material into said annular space proximally of the proximal end of the first follower thereby distally displacing the first follower;

e. continuing to introduce said molding material into the mold to continue the distal displacement of the first follower, thereby engaging the second follower and, thereafter, distally displacing the first and second follower off the first wire and into the second wire whereby there is formed the tip of the hollow article; and f. stripping the resulting hollow article from the first wire.

6. The process of manufacturing a hollow article which comprises:

a. providing a mold with a first wire longitudinally disposed therein and containing a follower disposed about the first wire in close abutment with both the first wire and inside wall of the mold, said follower maintaining the first wire spaced from the inside wall of the mold so as to define an annular space between the first wire and the inside of the mold;

b. providing a second wire spaced distally from said first wire and longitudinally aligned therewith;

c. positioning the first follower in the mold so that it spans at least 50% of the length of the first wire and at the same time bridges the space between the first wire and second wire;

d. introducing a molding material into said annular space proximally of the proximal end of the follower under a pressure sufficient to distally displace said follower;

e. continuing to introduce said molding material into said annular space until said follower is entirely displaced off said first wire and onto said second wire whereby there is formed a hollow article having a solid tip; and f. stripping the resulting hollow article from said first wire.

7. The process of claim 6 which further comprises:

a. sealing a set of gates in the mold by positioning the follower as in step c) above;

b. distally displacing the proximal end of the follower past the set of gates to unseal the set of gates; and c. thereafter introducing molding material into the annular space through the set of gates and continuing to distally displace the follower while material is molded around the first wire.

8. The process of manufacturing a hollow article which comprises:

a. providing a mold with a first wire longitudinally disposed therein and containing a follower disposed about the first wire in close abutment with both the first wire and inside wall of the mold, said follower maintaining the first wire spaced from the inside wall of the mold so as to define an annular space between the first wire and inside of the mold;

b. positioning the follower so that it seals a set of gates provided in the mold and spans at least about 50% of the length of the first wire;

c. introducing a molding material into said annular space proximally of the proximal end of the follower under pressure thereby distally displacing the first follower past the set of gates;

d. thereafter introducing the molding material into the annular space through the set of gates and continuing to distally displace the follower while material is molded around the first wire; and e. stripping the resulting hollow article from the first wire.

9. A process for producing a hollow article with a tip which comprises:

a. providing a mold with a drainage lumen wire longitudinally disposed therein, said drainage lumen wire having a widened cross section at its proximal end;
b. providing an inflation lumen wire longitudinally disposed in the mold, said inflation lumen wire also having a widened cross section at its proximal end;
c. positioning a first follower distally of the widened portions of the drainage lumen and inflation lumen wires, said first follower sealing a first set of gates in the mold;
d. positioning a second follower distally of said first follower, said second follower sealing a second set of gates in the mold, said first and second followers disposed about the drainage lumen and inflation lumen wires in close abutment with the drainage lumen and inflation lumen wires and inside wall of the mold, said first and second followers maintaining the drainage lumen and inflation lumen wires and inside wall of the mold spaced from each other so as to define a molding channel in the mold;
e. introducing molding material under pressure into the molding channel proximally of the proximal end of the first follower whereby material is molded around the widened portions of the drainage lumen and inflation lumen wires;
f. continuing introducing molding material into the molding channel thereby distally displacing the first follower and unsealing the first set of gates;
g. thereafter introducing molding material into the molding channel through the first set of gates and continuing to distally displace the first follower while molding material is molded around the drainage lumen and inflation lumen wires;
h. continuing the distal displacement of the first follower thereby also distally displacing the second follower and unsealing the second set of gates;
i. thereafter introducing material into the molding channel through the second set of gates and continuing to distally displace the first and second followers while material is molded around the drainage lumen and inflation lumen wires;
j. continuing the distal displacement of the first and second followers until both followers have been distally displaced from the inflation lumen and drainage lumen wires, thereby forming a hollow article with a solid tip;
k. stripping the resulting hollow article from the drainage and inflation lumen wires.

10. A process for producing a hollow article with a tip according to claim 9 which further comprises:
a. providing a third follower in close abutment with the drainage lumen and inflation lumen wires and inside wall of the mold;
b. positioning the third follower distally of the second follower, said third follower sealing a third set of gates in the mold;
c. continuing the distal displacement of the first and second followers thereby also distally displacing the third follower and unsealing the third set of gates;
d. thereafter introducing material into the molding channel through the third set of gates and continuing to distally displace the first, second and third followers while material is molded around the drainage lumen and inflation lumen wires.

11. A process for producing a hollow article with a solid tip according to claim 10 which further comprises:
a. providing a first receiving wire spaced distally from the drainage lumen wire and longitudinally aligned therewith;
b. providing a second receiving wire spaced distally from the inflation lumen wire and longitudinally aligned therewith;
c. bridging the space between the drainage lumen and inflation lumen wires and first and second receiving wires with a fourth follower, said fourth follower partially engaged with the drainage lumen and inflation lumen wires and the first and second receiving wires;
d. continuing the distal displacement of the first, second and third followers until the fourth follower is engaged and thereafter distally displacing the four followers off the drainage lumen and inflation lumen wires and onto the first and second receiving wires whereby there is formed a hollow article with a solid tip.

12. A process for producing a hollow article according to claim 9 which further comprises:
providing a first receiving wire spaced distally from the drainage lumen wires and longitudinally aligned therewith;
b. providing a second receiving wire spaced distally from the inflation lumen wire and longitudinally aligned therewith;
c. bridging the space between the drainage lumen and inflation lumen wires and first and second receiving wires with a third follower, said third follower partially engaged with the drainage lumen and inflation lumen wires and and first and second receiving wires;
d. continuing the distal displacement of the first and second followers until the third follower is engaged and thereafter distally displacing the three followers off the drainage lumen and inflation lumen wires and onto the first and second receiving wires whereby there is formed a hollow article with a solid tip.

13. The process of manufacturing a hollow article which comrises:
a. providing a mold with a first wire longitudinally disposed therein and containing first and second followers disposed about the first wire in close abutment with both the first wire and inside wall of the mold, said followers maintaining the first wire spaced from the inside wall of the mold so as to define an annular space between the first wire and the inside wall of the mold;
b. positioning the second follower proximally of the distal end of the mold and spaced distally from the first follower thereby sealing a gate provided in the mold;
c. introducing a molding material under pressure into said annular space proximally of the proximal end of the first follower thereby distally displacing the first follower;
d. continuing the distal displacement of the first follower thereby engaging the second follower and, thereafter, distally displacing both the first and second followers thereby unsealing the gate;
e. thereafter introducing molding material into the annular space through the gate to continue the distal displacement of the followers while material is molded around the first wire; and
f. stripping the resulting hollow article from the first wire.

14. The process of manufacturing a hollow article which comprises:

a. providing a mold with a first wire longitudinally disposed therein and containing a follower disposed about the first wire in close abutment with both the first wire and inside wall of the mold, said follower maintaining the first wire spaced from the inside wall of the mold so as to define an annular space between the first wire and inside of the mold;

b. positioning the follower so that it seals a gate, provided in the mold and spans at least about 50% of the length of the first wire;

c. introducing a molding material into said annular space proximally of the proximal side of the follower under pressure thereby distally displacing the first follower past the gate;

d. thereafter introducing the molding material into the annular space through the gate and continuing to distally displace the follower while material is molded around the first wire; and f. stripping the resulting hollow article from the first wire.

* * * * *

UNITED STATES PATENT AND TRADEMARK OFFICE
CERTIFICATE OF CORRECTION

PATENT NO. : 4,041,122
DATED : August 9, 1977
INVENTOR(S) : James R. Quick et al.

It is certified that error appears in the above-identified patent and that said Letters Patent are hereby corrected as shown below:

Abstract, line 19, "longidutinally" should be -- longitudinally --;

Column 1, line 2, "particulary" should be -- particularly --;

Column 11, line 19, "and" should be -- to --;

Column 12, line 32, "and" should be -- to --;

Column 12, line 41, "isinde" should be -- inside --;

Column 13, line 10, "lprovided" should be -- provided --;

Column 14, line 30, "usefull" should be -- useful --;

Column 18, line 22, before "providing" insert -- a. --;

Column 18, line 42, "comrises" should be -- comprises --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks